United States Patent [19]

Carter et al.

[11] Patent Number: 4,702,418

[45] Date of Patent: Oct. 27, 1987

[54] AEROSOL DISPENSER

[75] Inventors: Robert E. Carter, Auburndale; Donald R. Murphy, Wellesley, both of Mass.

[73] Assignee: Piezo Electric Products, Inc., Cambridge, Mass.

[21] Appl. No.: 773,677

[22] Filed: Sep. 9, 1985

[51] Int. Cl.$^4$ .............................................. B05B 3/14
[52] U.S. Cl. ...................................... 239/101; 239/4; 239/102.2; 310/328
[58] Field of Search ................ 239/4, 101, 102.2, 542, 239/596, 594, 102, 63, 68; 346/140 R; 431/1; 261/48; 310/328; 417/322

[56] References Cited

U.S. PATENT DOCUMENTS

| 3,387,607 | 6/1968 | Gauthier et al. | 239/102 |
| 3,679,132 | 7/1972 | Vehe et al. | 239/102 X |
| 3,700,169 | 10/1972 | Naydan et al. | 239/102 |
| 3,790,079 | 2/1974 | Berglund et al. | 239/102 |
| 3,852,773 | 12/1974 | Sicking et al. | 346/140 PD |
| 3,900,162 | 8/1975 | Titus et al. | 239/102 |
| 4,078,877 | 3/1978 | Friedl et al. | 431/1 |
| 4,209,131 | 6/1980 | Barash et al. | 239/68 |
| 4,285,352 | 8/1981 | McMahon et al. | 239/68 X |
| 4,388,627 | 6/1983 | Umezawa | 239/102 X |
| 4,465,234 | 8/1984 | Maehara et al. | 239/102 |
| 4,514,742 | 4/1985 | Suga et al. | 417/322 X |
| 4,516,140 | 5/1985 | Durkee et al. | 310/328 |
| 4,533,082 | 8/1985 | Maehara et al. | 431/1 |

FOREIGN PATENT DOCUMENTS 860877 9/1981 U.S.S.R. ............................. 239/102

OTHER PUBLICATIONS

"Ultrasonic Pulsing and Atomization Injector for Storable Liquid Maneuvering Engines" by Vance Jagna, Rockwell International, Rocketdyne Div.

Primary Examiner—Andres Kashnikow
Assistant Examiner—Kevin Patrick Weldon
Attorney, Agent, or Firm—Joseph S. Iandiorio; William E. Noonan

[57] ABSTRACT

An aerosol dispenser including a nozzle chamber for holding fluid to be dispensed and a diaphragm forming at least a portion of the chamber and having an aerosol dispensing nozzle disposed therein. The chamber includes a nozzle region proximate the nozzle and a larger reservoir region interconnected to the nozzle region. There is a restrictive passage for introducing fluid from the reservoir region to the nozzle region and restricting backflow from the nozzle region to the reservoir region. A driver, typically a piezoelectric bender, is provided to drive fluid from the reservoir region to the nozzle region and from the nozzle region through the nozzle to create an aerosol spray.

50 Claims, 9 Drawing Figures

AEROSOL DISPENSER

FIELD OF INVENTION

This invention relates to an aerosol dispenser and more particularly to an aerosol dispenser which employs a piezoelectric device for driving fluid through a nozzle to create an aerosol spray.

BACKGROUND OF INVENTION

A variety of fragrance dispensers are presently employed to overcome odors and dispense desired fragrances. Certain of these devices employ a container with a protruding wick. However, wick dispensers, even when reinforced with circulating fans, typically do not emit fragrance at a rate sufficient to mask truly offensive odors.

Pressurized aerosol dispensers, with pressure supplied either by a manual pump or a pressurized can, do emit an aerosol spray at a much higher rate than the wick dispenser. However, because the pressurized devices must be operated manually their effectiveness is limited. Their fragrance lasts for only a short duration and is typically dispensed or sprayed only after unpleasant odors are sensed.

An alternative fragrance dispenser employs a solid aluminum-clad fragrance disk which is heated electrically to evaporate the solid and thereby dispense the fragrance. Although this device emits a relatively high level of scent and is operated automatically, it requires line power and cannot be operated on low-voltage batteries. Furthermore, the replacement disks are relatively expensive and the disks themselves have a limited operational life of only approximately forty-five minutes.

SUMMARY OF INVENTION

It is therefore an object of this invention to provide an improved aerosol dispenser which operates on low voltage.

It is a further object of this invention to provide an aerosol dispenser which uses a piezoelectric driver to dispense the fragrance.

It is a further object of this invention to provide such a dispenser which is capable of operating on low voltage batteries.

It is a further object of this invention to provide such an aerosol dispenser which operates entirely automatically to dispense an aerosol at desired times or in response to sensed event, e.g., light, sound, odor or vibration.

It is a further object of this invention to provide such an aerosol dispenser which emits aerosol at a rate sufficient to effect a desired scent and/or mask offensive odors.

It is a further object of this invention to provide an aerosol dispenser which is relatively inexpensive and which exhibits extended operating life without frequent fluid refills or cartridge replacement.

This invention features an aerosol dispenser which includes a nozzle chamber for holding a fluid to be dispensed. A diaphragm forms at least a portion of the chamber and has an aerosol-dispensing nozzle disposed therein. The chamber includes a nozzle region proximate the nozzle and a larger reservoir region interconnected to the nozzle region. There are restrictive passage means for introducing fluid from the reservoir region to the nozzle region and restricting backflow from the nozzle region to the reservoir region. Means are further provided for driving fluid from the reservoir region to the nozzle region and from the nozzle region through the nozzle to create an aerosol spray.

In a preferred embodiment the means for driving includes piezoelectric driver means which typically includes piezoelectric bender means. The reservoir region may surround the nozzle region of the chamber. The bender means may form at least a portion of the wall of the chamber. The diaphragm preferably includes a concave section within which the nozzle is centrally located and may also include a convex portion which includes the nozzle and forms at least a part of the nozzle region. Typically, the nozzle is centrally located in the convex portion and such a convex portion is located within the concave section of the diaphragm. Alternatively, the diaphragm may include a concave section having a substantially flat bottom in which the nozzle is disposed. In such embodiments the restrictive passage means may be formed between the bottom of the concave section of the diaphragm and the bender means.

In alternative embodiments a flexible element may be interposed between the diaphragm and the bender means for dividing the reservoir region into first and second portions. Means may also be provided for transmitting bender deflection to flex the flexible element and pressurize the fluid in the nozzle chamber. Such means for transmitting may include some fluid in the first reservoir portion disposed between the bender means and the flexible element. Such fluid is pressurized by the bender deflection to flex the flexible element. Alternatively, the means for transmitting may include an actuator member extending between and attached to at least one of the bender means and the flexible element and being responsive to bender deflection for flexing the flexible element. The flexible member may be perforated so that the first and second portions communicate with each other. The restrictive passage means may be formed between flexible element and the bottom of the concave section of the diaphragm.

In another alternative embodiment the chamber may include a flexible wall portion, connected to the diaphragm and being responsive to deflection of the bender means for deflecting to pressurize the fluid in the nozzle region of the nozzle chamber. The diaphragm in the flexible wall portion is preferably integrally connected. The restrictive passage means may be formed between the flexible wall portion and the bottom of the concave portion of the diaphragm.

The means for driving may further include a pressurizing member with one end attached to the bender means and the opposite end disposed proximate the nozzle. The nozzle region of the chamber is located between the opposite end of the pressurizing member and the nozzle. The restrictive passage may be formed between the opposite end of the pressurizing member and the diaphragm. The opposite end of the pressurizing member may include a recessed region forming at least a part of the nozzle region of the chamber. In such embodiments the diaphragm may be substantially flat.

The restrictive passage means may include valve means for introducing fluid from the reservoir region to the nozzle region and restricting backflow from the nozzle region to the reservoir region. Such valve means may include a unidirectional valve for controlling flow through the restrictive passage means.

The bender means may include a ceramic acoustic tone transducer. The nozzle may be generally conically shaped and it is preferred that the nozzle region be no larger than 0.1 cubic centimeter. The dispenser may further include a storage chamber for holding fluid to be dispensed and channel means connecting the storage chamber in the reservoir region of the nozzle chamber.

Means may be provided for controlling the operation of the bender means. Such means for controlling typically include timer means for operating the bender means at predetermined times and/or sensor means for sensing a predetermined physical parameter. There are means responsive to such sensor means for operating the bender means when the predetermined physical parameter is sensed. Means may also be provided for sensing that the fluid in the nozzle has dropped below a predetermined level. Means, responsive to said means for detecting, may also be provided for indicating that the fluid level has dropped below the predetermined level. The means for detecting may include a pair of electrodes for sensing the presence of the fluid between them.

DISCLOSURE OF PREFERRED EMBODIMENT

Other objects, features and advantages will occur from the following description of a preferred embodiment and the accompanying drawings, in which.

Figure 1:
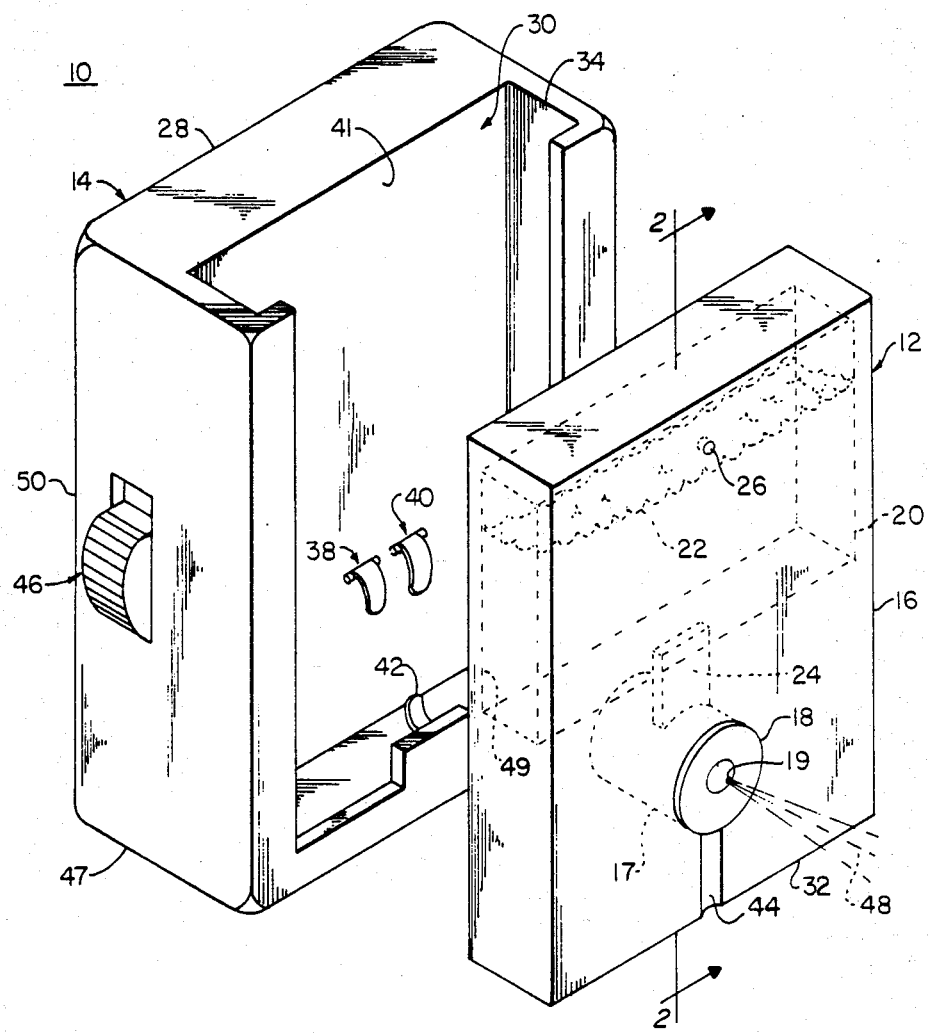
FIG. 1 is an axonometric view of a replaceable cartridge which includes the aerosol dispenser according to this invention and a power supply unit which receives the replaceable cartridge.

An aerosol dispenser according to this invention may be accomplished with a nozzle chamber for holding fluid to be dispensed. The chamber includes a diaphragm, which is typically a 2-5 mil thick shim composed of stainless steel or similar material. An aerosol-dispensing nozzle is disposed in the diaphragm. Preferably, the nozzle is generally conically shaped. The nozzle chamber includes a nozzle region proximate the nozzle and a larger reservoir region interconnected to, and preferably surrounding, the nozzle region. Typically, the nozzle region is no larger than 0.1 cubic centimeter.

The diaphragm may include a concave section and a convex portion centrally disposed in the concave section. The nozzle is preferably located centrally in the convex portion. There is a restrictive passage means for introducing fluid from the reservoir region to the nozzle region and restricting backflow from the nozzle region to the reservoir region.

Means which preferably include piezoelectric bender means are provided for driving fluid from the reservoir region to the nozzle region and from the nozzle region through the nozzle to create an aerosol spray. A preferred bender is a ceramic acoustic-tone transducer (CATT) disk. A typical CATT disk includes a brass shim stock disk which is, for example, 1⅜ inches in diameter and 10 mils thick. A one-inch diameter, 10 mils thick piezoelectric wafer disk is bonded by any acceptable means to the shim stock and electrodes are attached to the shim stock and to the opposite side of the piezoelectric wafer. The shim stock may itself serve as one of the electrodes. The resonant frequency of such CATT disks is typically from 2 to 4 KHz.

The CATT disk or other bender may form at least one of the walls of the nozzle chamber. The diaphragm typically forms another wall and the remaining walls may be composed of ABS plastic or similar material. In such embodiments the restrictive passage means may be formed between the bender and the bottom of the concave section of the diaphragm.

In alternative embodiments a very thin flexible member, composed of, for example, 2 mils thick saran plastic or similar material is interposed between the diaphragm and the bender to divide the reservoir region into first and second portions. There are means for transmitting bender deflection to flex the flexible member and pressurize the fluid in the nozzle region of the nozzle chamber. The means for transmitting may include some of the fluid in the first reservoir portion between the bender means and the flexible means. When the bender is deflected, that fluid is pressurized to flex the flexible member. In turn, the fluid in the nozzle region is pressurized. Alternatively, an actuator member may extend between and be attached to one of the bender means and the flexible member. The actuator means responds to deflection of the bender to flex the flexible member. The flexible member is typically perforated so that the first and second portions of the reservoir region can communicate with each other. In such embodiments the restrictive passage is typically formed between the flexible member and the bottom of the concave portion of the diaphragm.

In still another embodiment an integral flexible wall and diaphragm may be provided and the bender means may be disposed outside of the nozzle chamber. The restrictive means in such devices are typically formed between the flexible wall portion and the bottom of the concave portion of the diaphragm.

A further embodiment includes valve means for introducing fluid from the reservoir region to the nozzle region and for restricting backflow from the nozzle region to the reservoir region. Such valve means may include a unidirectional valve such as a flapper, check or ball valve.

In certain embodiments the convex diaphragm section may be omitted and a concave portion may be employed which has a substantially flat central region in which the nozzle is disposed. In yet another embodiment the concave diaphragm may be eliminated and a pressurizing member attached at one end to the bender means. The other end of the pressurizing member is proximate the nozzle so that the nozzle region is located between the opposite end of the pressurizing member and the nozzle. The restrictive passage means are formed between the opposite end of the pressurizing member and the diaphragm. At least a part of the nozzle region may be formed by a recessed region within the opposite end of the pressurizing member.

The bender means may be operated to generate a pressure in the nozzle region at predetermined times or in response to predetermined sounds, odors, light, or other sense parameters. A system may also be provided for detecting and indicating that the fluid in the nozzle chamber has dropped below a predetermined level and requires refilling.

It is preferred that the bender means be operated by application of a relatively low voltage (for example, 3-9 volts). This permits the dispenser to be battery-operated and allows it to be conveniently carried and operated.

There is shown in FIG. 1 a piezoelectric aerosol dispenser 10 which includes a replaceable cartridge 12 and a permanent power unit 14. Cartridge 12 includes a plastic body 16 within which is disposed a nozzle chamber 17, having a diaphragm 18. A nozzle 19 is centrally located in diaphragm 18. Cartridge 12 further includes a storage chamber 20 for containing fragrance generating fluid 22 to be dispensed. A channel 24 conducts fluid 22 from storage chamber 20 to nozzle chamber 17. A vent 26 extends from storage chamber 20 and maintains the interior of chamber 20 at atmospheric pressure so that fluid 22 gravitates downwardly through channel 24 to nozzle chamber 17.

Figure 9:
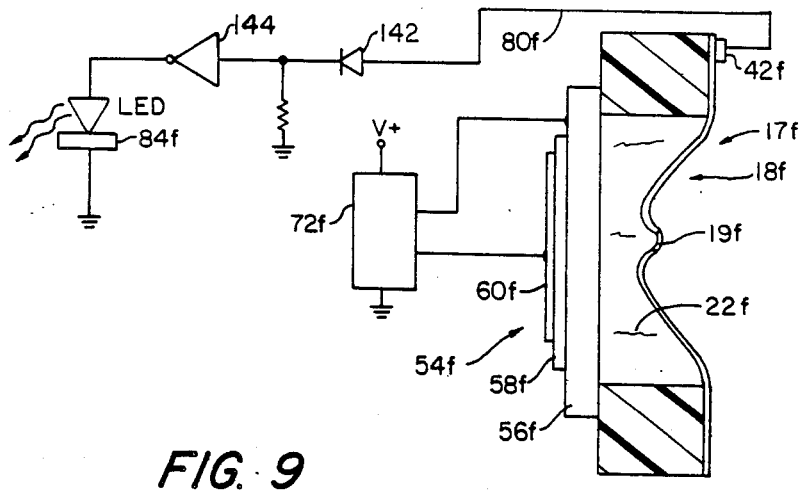
FIG. 9 is a schematic view of a circuit for detecting and indicating that the fluid in the nozzle chamber has dropped below a predetermined level.

Power unit 14 is typically composed of injection molded plastic and includes a housing 28 which contains a power source and control and level detector circuitry, not shown in FIG. 1 but discussed in connection with FIGS. 3 and 9. The power unit further includes a recess 30 into which cartridge 12 is slidably installed by inserting end 32 through opening 34 and sliding the cartridge downwardly in recess 30. Contacts 38 and 40 extend from wall 41 and engage nozzle chamber 17 as set forth below. Contact 42 is slidably received through slot 44 of cartridge body 16 and engages the diaphragm 18 of nozzle chamber 17. Contact 42 is employed in the fluid level sensing circuit as described more fully below.

After cartridge 12 has been installed in recess 30 the dispenser is activated by turning on switch 46. This energizes contacts 38 and 40 which transmit power as described in connection with FIG. 2 to drive fluid through nozzle 19 of diaphragm 18 and dispense an aerosol spray 48. In order to replace fluid which has been dispensed unit 14 is stood on its end 47. This enables fluid 22 to gravitate from storage chamber 20 through channel 24 to nozzle chamber 17. By constructing channel 24 sufficiently close to surface 49 of storage chamber 20, dispenser 10 can also be operated while lying on its surface 50.

Figure 2:
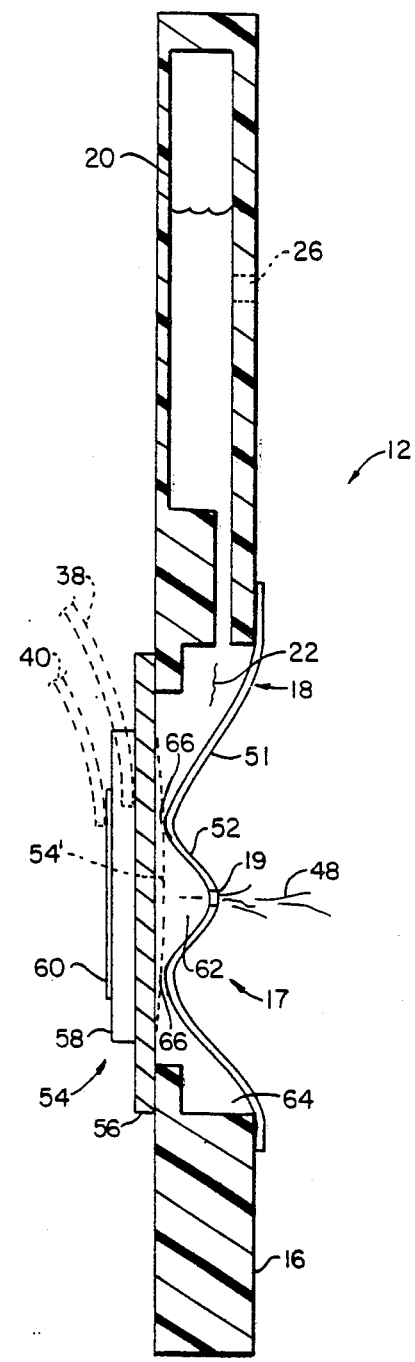
FIG. 2 is a cross-sectional view taken along line 2—2 of FIG. 1 of one embodiment of the aerosol dispenser.

As shown in FIG. 2 diaphragm 18 of nozzle chamber 17 includes a concave section 51 within which is centrally located a convex section 52. Nozzle 19 is centrally located within convex section 52. One wall of nozzle chamber 17 is formed by a piezoelectric bender 54 which includes a thin, typically metallic element 56 bonded to the surface of body 16 and a piezoceramic layer 58 bonded on one side to metallic element 56. An electrode 60 is applied to the opposite side of piezoceramic layer 58. Both diaphragm 18 and bender 54 are secured to cartridge body 16 by epoxy or other adhesive agent. Nozzle chamber 17 includes a nozzle region 62, which is typically less than 0.1 cubic centimeter in volume, formed under convex section 52 of diaphragm 18 and a larger reservoir region 64 which surrounds nozzle region 62. A very narrow (e.g., 0 to 40 mils) restrictive passage 66 is formed between the bottom of concave section 51 and bender 54. This restrictive passage interconnects reservoir region 64 and nozzle region 62.

When cartridge 12 is inserted in the power unit as shown in FIG. 1, contacts 38 and 40, shown in phantom in FIG. 2, engage metallic element 56 (which serves as one electrode of bender 54) and electrode 60, respectively. Third contact 42 engages metallic diaphragm 18. In operation, pulses are applied through contacts 38 and 40 to bender 54 and the bender is caused to alternately deflect to position 54' as the voltage is applied and relax to its initial state as the voltage is removed. As a result, pressure is increased in nozzle region 62 and fluid 22 is forced through nozzle 19 to create an aerosol spray 48.

As fluid is ejected from nozzle region 62 through nozzle 19 additional fluid drains into nozzle chamber 17 from storage chamber 22 through channel 24. This replacement fluid is introduced from reservoir region 64 to nozzle region 62 through restrictive passage 66. However, the restrictive passage 66 is sufficiently narrow so that it restricts the backflow of fluid 22 from nozzle region 62 to reservoir region 64 when bender 54 is deflected to position 54'. This results in a unidirectional fluid flow from storage chamber 22 through channel 24, reservoir region 64, passage 66, and nozzle region 62 and out through nozzle 19.

Figure 3:
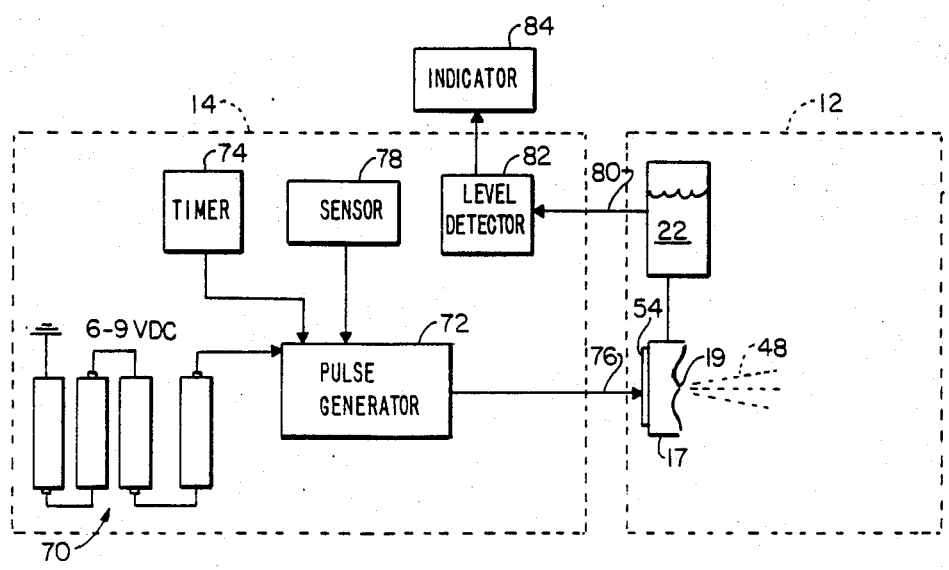
FIG. 3 is a schematic diagram of a power supply and control circuitry for automatically operating the aerosol dispenser of FIG. 2.
Figure 5:
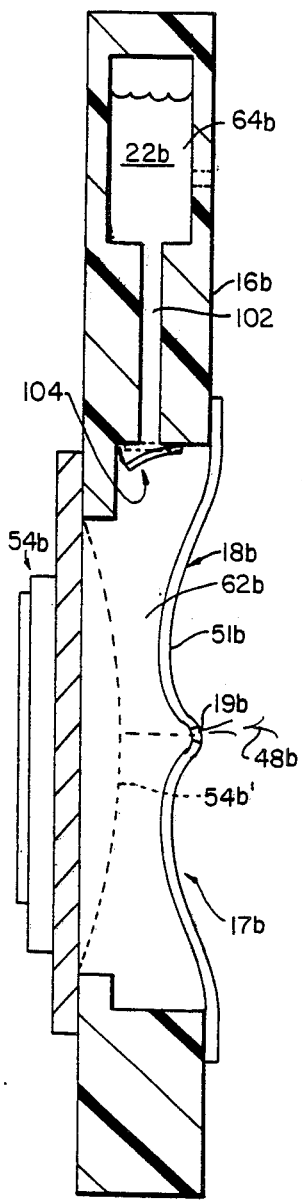
FIG. 5 is a view similar to that of FIG. 2 of a further alternative embodiment of the aerosol dispenser which includes a one-way flap valve.
Figure 4:
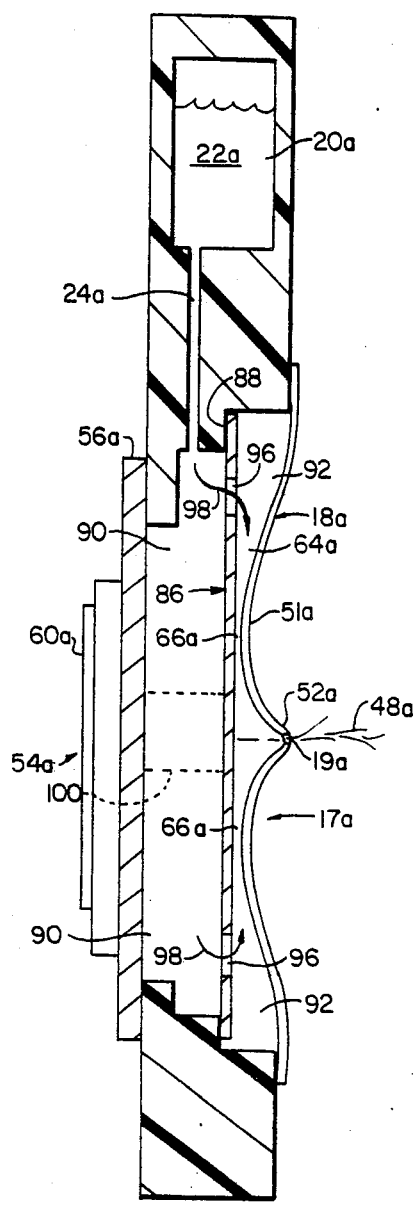
FIG. 4 is a view similar to that of FIG. 2 of an alternative embodiment of a low-voltage aerosol dispenser which employs a perforated flexible element in the nozzle chamber.
Figure 6:
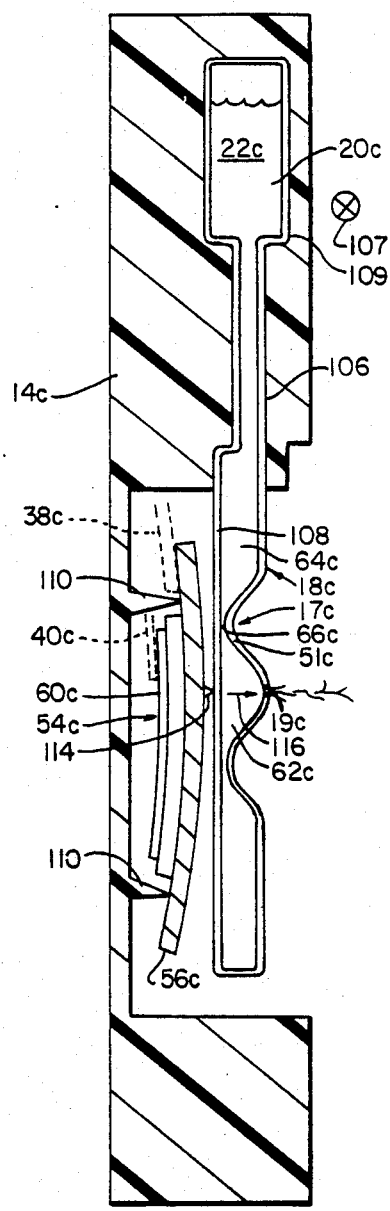
FIG. 6 is a view similar to that of FIG. 2 of an alternative aerosol dispenser in which the nozzle chamber is formed from an integral diaphragm and flexible wall.
Figure 7:
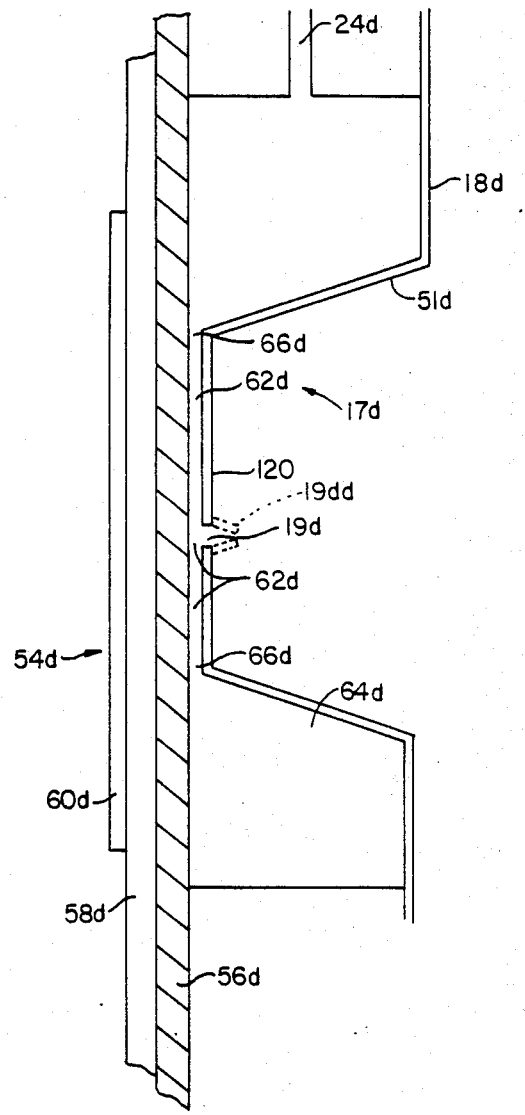
FIG. 7 is a view similar to that of FIG. 2 of an additional alternative aerosol dispenser employing a generally concave diaphragm having a substantially flat bottom.
Figure 8:
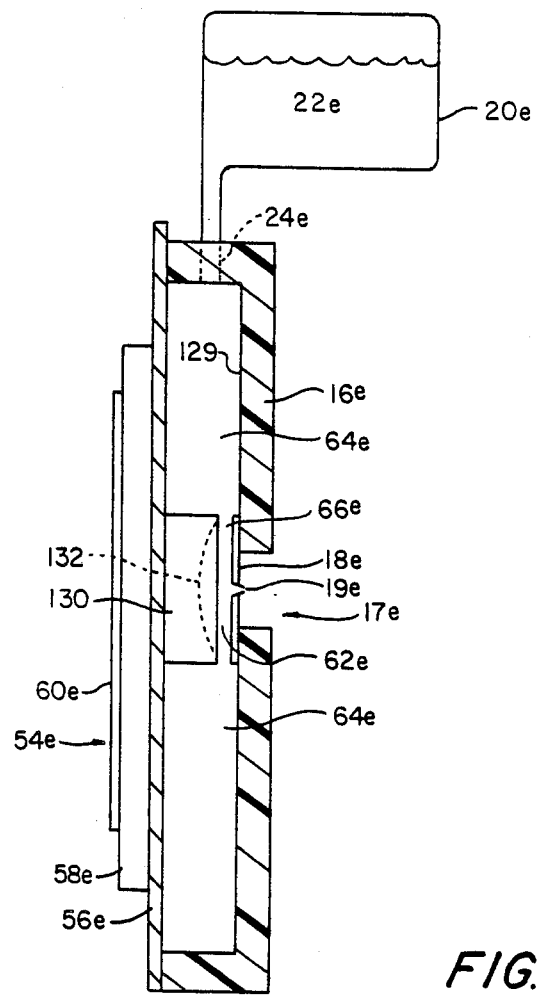
FIG. 8 is a cross-sectional view of an another alternative aerosol dispenser which utilizes a substantially flat diaphragm.

As shown in the schematic diagram of FIG. 3, power unit 14 includes a low-voltage power source 70 which consists of four 1.5 volt cells that provide six volts of direct current to pulse generator 72. Timer 74 is programmed to activate pulse generator 72 at, for example, 15-minute intervals for a desired period of time. Pulse generator 72 when so activated provides a pulsed signal, at for example one second intervals, over line 76 to bender 54. The bender is activated to pressurize fluid 22 in nozzle chamber 17 so that aerosol spray 48 is emitted through nozzle 19.

A sensor 78 may also be provided to activate pulse generator 72 in response to the detection of a predetermined light, odor, sound, etc. The pulse generator may then be operated either for a predetermined time or until the sensed event ceases, e.g., the light is turned off or the odor subsides.

As is more fully described below in connection with FIG. 9, a signal, indicative of the level of fluid 22, is provided via line 80 to a level detector 82. When the sensed fluid level falls below a predetermined amount, a signal is provided to indicator 84 which provides a visual or audio signal indicating that the fluid needs to be refilled and that cartridge 12 requires replacement.

An alternative nozzle chamber **17*a*, FIG. 4, includes a diaphragm 18*a* having a concave section 51*a* and a central convex section 52*a*. A thin flexible element 86 mounted on a ledge 88 within chamber 17*a* divides reservoir region 64*a* of the chamber into a first portion 90 and a second portion 92. Element 86 is disposed proximate, e.g., 5 to 10 mils from, the bottom of concave section 51*a* and forms a restrictive passage 66*a* which interconnects the first portion 92 of reservoir region 64*a* with nozzle region 62*a*. Fluid 22*a* from the storage chamber 20*a* is introduced through channel 24*a*** to first portion 90 of reservoir region 64*a*. Element 86 is provided with perforations 96 which permit the first and second portions of reservoir region 92 to communicate with each other and fluid to pass into portion 92.

Pulses are applied to electrodes 60*a* and 56*a* of bender 54*a* as previously described to periodically deflect bender 54*a*. This causes pressure to build up in the fluid within portion 90 and this pressure eventually causes element 86 to flex and generate pressure in nozzle region 62 so that fluid is driven through nozzle 19*a* and emitted as an aerosol spray 48*a*. Alternatively, deflection of bender 54*a* may be transmitted to element 86 by an actuating member 100 (in phantom) interconnected between bender 54*a* and element 86. In either embodiment the fluid from portion 90 travels in the direction of arrows 98 through perforations 96 and then through restrictive passage 66*a* to replace the fluid driven through the nozzle 19*a*. Again, the restrictive passage 66*a* restricts backflow of fluid from nozzle region 62*a* when element 86 is flexed.

In another embodiment, FIG. 5, bender 54*b* is not proximate the bottom of concave portion 51*b* of diaphragm 18*b* and a restrictive passage is not formed between the bender and the concave portion of the diaphragm. Rather, nozzle region 62*b* and reservoir region 64*b* are interconnected by a restrictive passage 102 which extends through cartridge body 16*b*. In this embodiment, unlike the previously described embodiments, the reservoir region does not surround the nozzle region. Rather, it occupies the location occupied by storage chambers 20, 20*a* in the embodiments of FIGS. 2 and 4. A unidirectional valve 104 is provided at the mouth of channel 102 where it meets nozzle region 62*b*.

When bender 54*b* is in the relaxed condition, as shown, valve 104 opens to permit fluid 22*b* to enter nozzle region 62*b*. However, when bender 54*b* is deflected to position 54*b*' valve 104 closes to prevent the backflow of fluid 22*b* from nozzle region 62*b* to reservoir 64*b*. Instead, the fluid is driven through nozzle 19*b* and emitted as an aerosol spray 48*b*.

As shown in FIG. 6, bender 54*c* may be mounted in the power unit 14*c* rather than with the dispenser. Nozzle chamber 17*c* and reservoir 22*c* together form a replaceable unit which is inserted in the direction of arrow 107 into a slot 109 in the power unit 14*c*. Chamber 17*c* includes a diaphragm 18*c*, constructed as previously described, and an opposite flexible wall 108 which is integrally connected with diaphragm 18*c*. Restrictive passage 66*c* is formed between wall 108 and concave portion 51*c* of diaphragm 18*c*. Bender 54*c* is mounted on a ring-shaped ridge 110 and its electrodes 56*c* and 60*c* are engaged by contacts 38*c* and 40*c*. An actuator element 114 is mounted to the top of bender 54*c*.

When actuating voltage is applied to bender 54*c* the bender deflects and actuator element 114 bears on and flexes flexible wall 108 of chamber 18*c*. Wall 108 flexes inwardly as indicated by arrow 116 to create a pressure in nozzle region 62*c* and drive fluid through nozzle 19*c*. Restrictive passage 66*c* permits fluid 22*c* to be introduced from reservoir region 64*c* but restricts the backflow of fluid from nozzle region 62*c* to reservoir region 64*c* when wall 108 is flexed inwardly.

In another construction nozzle chamber 17*d*, FIG. 7, includes a diaphragm 18*d* having a concave section 51*d* with a flat bottom 120. Bender 54*d* forms the opposite wall of chamber 17*d*. Nozzle region 62*d* is formed between the diaphragm and the nozzle 19*d* and is surrounded by a reservoir region 64*d*. A channel 24*d* interconnects the reservoir region with a storage chamber, not shown. Restrictive passage 66*d* interconnecting reservoir region 64*d* and nozzle region 62*d* again restricts backflow of fluid into the reservoir region when bender 54*d* is deflected.

Nozzle 19*d*, as well as the nozzle in any of the embodiments of this invention, may be substantially flat. Alternatively, as shown in phantom 19*dd* the diaphragm may be conically tapered to a nozzle. Either construction may be used to generate an aerosol spray as the fluid is driven through the nozzle opening.

As shown in FIG. 8, a substantially flat diaphragm 18*e* may be secured, such as by a suitable adhesive, to the cartridge body 16*e*. That diaphragm and wall 129 of body 16*e* form one wall of nozzle chamber 17*e*. The opposite wall is formed by bender 54*e*. Mounted to the bender is a pressurizing member 130 which may be provided with a recess 132 in its surface proximate diaphragm 18*e*. Nozzle region 62*e* is disposed between recessed surface 132 of pressurizing member 130 and diaphragm 18*e*. Reservoir region 64*e* surrounds the pressurizing member 130 and the nozzle region 62*e* and is interconnected to the nozzle region by a restricted passage 66*e*. Storage chamber 20*e* filled with fluid 22 is connected to reservoir region 64*e* by channel 24*e*.

When pulsed actuating voltage is applied to bender 54*e*, the bender is deflected as previously described and pressurizing member 130 is driven toward diaphragm 18*e*. Fluid within nozzle region 62*e* is pressurized and driven through nozzle 19*e* to be emitted as an aerosol spray. Passage 66*e* again restricts backflow fluid into reservoir region 64*e*.

A level detector circuit, FIG. 9, is provided to indicate when the fluid level is low and the cartridge needs to be replaced. The fluid 22*f* acts as one of the actuating electrodes. Pulse generator 72*f* provides 2–4 KHz pulses to bender 54*f* which causes the bender to deflect and fluid to be emitted through nozzle 19*f* of diaphragm 18*f*, as previously described. Contact 42*f* engages metal diaphragm 18*f*. The fluid 22*f* in chamber 17*f* provides a conductive path between element 56*f* and contact 42*f*. When the fluid level in nozzle chamber 17*f* is above a predetermined level, a first signal is provided over line 80*f* through diode 142 to inverter 144. In response to this signal the inverter provides a low output which is insufficient to activate an indicator LED 84*f*. This indicates that sufficient fluid is present. However, when the fluid level in chamber 17*f* drops so that fluid no longer entirely fills the space between diaphragm 18*f* and bender 54*f*, the resistance increases markedly. When next a signal is provided to inverter 144 it responds by providing a high output to activate LED 84*f* and indicate that the fluid must be replenished or the cartridge must be replaced.

Although specific features of the invention are shown in some drawings and not others, this is for convenience only as each feature may be combined with any or all of the other features in accordance with the invention.

Other embodiments will occur to those skilled in the art and are within the following claims:

What is claimed is:

1. A piezoelectric aerosol dispenser comprising:

a nozzle chamber for holding a fluid to be dispensed and a diaphragm forming at least a portion of said chamber and having an aerosol dispensing nozzle disposed therein, said chamber including a nozzle region proximate said nozzle and a larger reservoir region interconnected to said nozzle region;

backflow restrictive means for introducing fluid from said reservoir region to said nozzle region and restricting backflow from said nozzle region to said reservoir region, said backflow restrictive means formed in part by said diaphragm; and means, including piezoelectric bender means, for driving fluid from said reservoir to said nozzle region and from said nozzle region through said nozzle to create an aerosol spray.

2. The aerosol dispenser of claim 1 in which said reservoir region surrounds said nozzle region of said chamber.

3. The dispenser of claim 1 in which said bender means forms at least a portion of said chamber.

4. The aerosol dispenser of claim 1 in which said diaphragm has a convex portion which includes said nozzle and forms at least a part of said nozzle region.

5. The dispenser of claim 4 in which said nozzle is generally centrally located in said convex portion.

6. The aerosol dispenser of claim 1 in which said diaphragm further includes a concave section within which said nozzle is centrally located.

7. The dispenser of claim 6 in which said concave diaphragm section includes a central convex portion which includes said nozzle and forms at least a part of said nozzle region.

8. The dispenser of claim 6 further including a flexible element interposed between said diaphragm and said bender means and dividing said reservoir region into first and second portions and means for transmitting bender deflection to flex said flexible element and pressurize said fluid in said nozzle region of said nozzle chamber.

9. The dispenser of claim 8 in which said means for transmitting includes fluid in said first reservoir portion disposed between said bender means and said flexible element and being pressurized by said bender deflection to flex said flexible element.

10. The dispenser of claim 8 in which said means for transmitting includes an actuator member extending between and attached to at least one of said bender means and said flexible element and being responsive to bender deflection for flexing said flexible element.

11. The dispenser of claim 8 in which said flexible element is perforated so that said first and second portions of said reservoir region communicate with each other.

12. The dispenser of claim 6 in which said chamber includes a flexible wall portion, connected to said diaphragm, responsive to deflection of said bender means for flexing to pressurize said fluid in said nozzle region of said nozzle chamber.

13. The dispenser of claim 12 in which said diaphragm and said flexible wall portion are integrally connected.

14. The dispenser of claim 1 in which said diaphragm includes a concave section having a substantially flat bottom in which said nozzle is disposed.

15. The dispenser of claim 1 in which said means for driving further includes a pressurizing member attached at one end to said bender means the opposite end being proximate to said nozzle, said nozzle region of said chamber being located between the opposite end of said pressurizing member and said nozzle.

16. The dispenser of claim 15 in which the opposite end of said pressurizing member includes a recessed region forming at least a part of the nozzle region of said chamber.

17. The dispenser of claim 15 in which said diaphragm is substantially flat.

18. The dispenser of claim 1 in which said bender means includes a ceramic acoustic tone transducer.

19. The dispenser of claim 1 in which said nozzle is generally conically shaped.

20. The dispenser of claim 1 in which said nozzle is substantially flat.

21. The dispenser of claim 1 further including a storage chamber for holding fluid to be dispensed and channel means connecting said storage chamber and said reservoir region of said nozzle chamber.

22. The dispenser of claim 1 in which said nozzle region of said nozzle chamber is no larger than 0.1 cubic centimeter.

23. The dispenser of claim 1 further including means for controlling the operation of said bender means.

24. The dispenser of claim 23 in which said means for controlling includes timer means for operating said bender means at predetermined times.

25. The dispenser of claim 23 in which said means for controlling includes sensor means for sensing a predetermined physical parameter and means responsive to said sensor means for operating said bender means when said predetermined physical parameter is sensed.

26. The dispenser of claim 1 further including means for detecting that the fluid in said nozzle chamber has dropped below a predetermined level and means, responsive to said means for sensing, for indicating that the fluid level has dropped below said predetermined level.

27. The dispenser of claim 26 in which said means for detecting includes a pair of electrodes for sensing the presence of said fluid between them.

28. A piezoelectric aerosol dispenser comprising:

a nozzle chamber for holding a fluid to be dispensed and a generally concave diaphragm forming at least a portion of said chamber and having a central convex portion with an aerosol forming nozzle disposed therein, said convex portion forming a nozzle region in said chamber, said nozzle chamber further including a larger reservoir region interconnected with said nozzle region;

backflow restrictive means for introducing fluid from said reservoir region to said nozzle region, said backflow restrictive means formed is part by said diaphragm; and means, including piezoelectric bender means, for driving fluid from said reservoir region to said nozzle region and from said nozzle region through said nozzle to create an aerosol spray, said backflow restrictive means being responsive to flexing of said bender means for narrowing the passage connecting said nozzle region and said reservoir region to restrict backflow from said nozzle region to said reservoir region.

29. A piezoelectric aerosol dispenser comprising:

a nozzle chamber for holding a fluid to be dispensed and a generally concave diaphragm forming at least a portion of said chamber and having a central convex portion with an aerosol forming nozzle disposed therein, said convex portion forming a nozzle region in said chamber, said chamber further including a larger reservoir region interconnected with said nozzle region;

backflow restrictive means for introducing fluid from said reservoir region to said nozzle region, said backflow restrictive means formed in part by said diaphragm;

means, including piezoelectric bender means, for driving fluid from said reservoir region to said nozzle region and from said nozzle region through said nozzle to create an aerosol spray, said backflow restrictive means being responsive to flexing of said bender means for narrowing the passage connecting said nozzle region and said reservoir region to restrict backflow from said nozzle region to said reservoir region;

a flexible member interposed between said diaphragm and said bender means; and means for transmitting bender deflection to flex said flexible member and pressurize said fluid in said nozzle region.

30. A piezeoelectric aerosol dispenser comprising:

a nozzle chamber for holding a fluid to be dispensed and a generally concave diaphragm forming at least a portion of said chamber and having a central convex portion with an aerosol forming nozzle disposed therein, said convex portion forming a nozzle region in said chamber, said nozzle chamber further including a larger reservoir region interconnected with said nozzle region and a flexible wall portion connected to said diaphragm;

backflow restrictive means for introducing fluid from said reservoir region to said nozzle region, said backflow restrictive means formed in part by said diaphragm; and means, including piezeoelectric bender means, for driving fluid from said reservoir region to said nozzle region and from said nozzle region through said nozzle to create an aerosol spray said flexible wall portion being responsive to deflection of said bender means for flexing to pressurize said fluid in said nozzle region of said chamber, and said backflow restrictive means being responsive to flexing of said bender means for narrowing the passage connecting said nozzle region and said reservoir region to restrict backflow from said nozzle region to said reservoir region.

31. A piezoelectric aerosol dispenser comprising:

a nozzle chamber for holding a fluid to be dispensed and a generally concave diaphragm forming at least a portion of said chamber and including a substantially flat central region with an aerosol dispensing nozzle disposed therein, said chamber including a nozzle region and a larger reservoir region interconnected to said nozzle region;

backflow restrictive means for introducing fluid from said reservoir region to said nozzle region, said backflow restrictive means formed in part by said diaphragm; and means, including piezeoelectric bender means which forms at least a portion of the wall of said chamber, for driving fluid from said reservoir region to said nozzle region and from nozzle region through said nozzle to create an aerosol spray, said backflow restrictive means being responsive to flexing of said bender means for narrowing the passage connecting said nozzle region and said reservoir region to restrict backflow from said nozzle region to said reservoir region.

32. A piezoelectric aerosol dispenser comprising:

a nozzle chamber for holding a fluid to be dispensed and a substantially flat diaphragm forming at least a portion of said chamber and having an aerosol dispensing nozzle disposed therein; said chamber including a nozzle region and a larger reservoir region interconnected with said nozzle region;

backflow restrictive means for introducing fluid from said reservoir region to said nozzle region, said backflow restrictive means formed in part by said diaphragm; and means for driving fluid from said reservoir region to said nozzle region and from said nozzle region through said nozzle to create an aerosol spray, including piezoelectric bender means and a pressurizing member attached at one end to said bender means, the opposite end being proximate said nozzle, said nozzle region being located between the opposite end of said pressurizing member and said nozzle, and said backflow restrictive means being responsive to flexing of said bender means for narrowing the passage connecting said nozzle region and said reservoir region to restrict backflow from said nozzle region to said reservoir region.

33. An aerosol dispenser comprising:

a nozzle chamber for holding a fluid to be dispensed and a diaphragm forming at least a portion of said chamber and having an aerosol dispensing nozzle disposed therein, said chamber including a nozzle region proximate said nozzle and a larger reservoir region interconnected to said nozzle region;

backflow restrictive means for introducing fluid from said reservoir region to said nozzle region and restricting backflow from said nozzle region to said reservoir region, said backflow restrictive means formed in part by said diaphragm; and means for driving fluid from said reservoir region to said nozzle region and from said nozzle region through said nozzle to create an aerosol spray.

34. The dispenser of claim 33 in which said means for driving includes piezoelectric driver means.

35. The dispenser of claim 34 in which said piezoelectric driver means includes piezoelectric bender means.

36. The dispenser of claim 33 in which said reservoir region surrounds said nozzle region of said chamber.

37. The dispenser of claim 33 in which said diaphragm has a convex portion which includes said nozzle and forms at least a part of said nozzle region.

38. The dispenser of claim 37 in which said nozzle is generally centrally located in said convex portion.

39. The dispenser of claim 33 in which said diaphragm further includes a concave section within which said nozzle is centrally located.

40. The dispenser of claim 39 in which said concave diaphragm section includes a central convex portion which includes said nozzle and forms at least a part of said nozzle region.

41. The dispenser of claim 33 in which said nozzle region of said nozzle chamber is no larger than 0.1 cubic centimeter.

42. The dispenser of claim 37 in which said nozzle is generally conically shaped.

43. The dispenser of claim 33 in which said nozzle is substantially flat.

44. A piezoelectric aerosol dispenser comprising:

a nozzle chamber for holding a fluid to be dispensed and a diaphragm forming at least a portion of said chamber and having an aerosol dispensing nozzle disposed therein, said chamber including a nozzle region proximate said nozzle and a larger reservoir region interconnected to said nozzle region, backflow restrictive means for introducing fluid from said reservoir region to said nozzle region, said backflow restrictive means formed in part by said diaphragm; and means, including piezeoelectric bender means, for driving fluid from said reservoir region to said nozzle region and from said nozzle region through said nozzle to create an aerosol spray, said backflow restrictive means being responsive to flexing of said bender means for narrowing the passage connecting said nozzle region and said reservoir region to restrict backflow from said nozzle region to said reservoir region.

45. A piezoelectric aerosol dispenser comprising:

a nozzle chamber for holding a fluid to be dispensed and a diaphragm forming at a portion of said chamber and having an aerosol dispensing nozzle disposed therein, said chamber including a nozzle region proximate said nozzle and a larger reservoir region interconnected to said nozzle region;

backflow restrictive means for introducing fluid from said reservoir region to said nozzle region, said backflow restrictive means formed in part by said diaphragm; and means for driving fluid from said reservoir region to said nozzle region and from said nozzle region through said nozzle to create an aerosol spray, said backflow restrictive means being responsive to said means for driving for constricting the passage connecting said nozzle region and said reservoir region to restrict backflow from said nozzle region to said reservoir region.

46. A piezoelectric aerosol dispenser comprising:

a nozzle chamber for holding a fluid to be dispensed and diaphragm forming at least a portion of said chamber and having an aerosol dispensing nozzle disposed therein, said diaphragm further including a concave section within which said nozzle is centrally located, said chamber including a nozzle region proximate said nozzle and a larger reservoir region interconnected to said nozzle region;

backflow restrictive means, formed between the bottom of the concave section of said diaphragm and said bender means, for introducing fluid from said reservoir region to said nozzle region and restricting backflow from said nozzle region to said reservoir region; and means, including piezoelectric bender means, for driving fluid from said reservoir region to said nozzle region and from said nozzle region through said nozzle to create an aerosol spray.

47. A piezoelectric aerosol dispenser comprising:

a nozzle chamber for holding a fluid to be dispensed and diaphragm forming at least a portion of said chamber and having an aerosol dispensing nozzle disposed therein, said diaphragm further including a concave section within which said nozzle is centrally located, said chamber including a nozzle region proximate said nozzle and a larger reservoir region interconnected to said nozzle region;

means, including piezoelectric bender means, for driving fluid from said reservoir region to said nozzle region and from said nozzle region through said nozzle to create an aerosol spray;

a flexible element interposed between said diaphragm and said bender means and dividing said reservoir region into first and second portions and means for transmitting bender deflection to flex said flexible element and pressurize said fluid in said nozzle region of said nozzle chamber; and restrictive passage means, formed between said flexible element and the bottom of the concave section of said diaphragm, for introducing fluid from said reservoir region to sasid nozzle region and restricting backflow from said nozzle region to said reservoir region.

48. A piezoelectric aerosol dispenser comprising:

a nozzle chamber for holding a fluid to be dispensed and a diaphragm forming at least a portion of said chamber and having an aerosol dispensing nozzle disposed therein, said diaphragm further including a concave section within which said nozzle is centrally located, said chamber including a nozzle region proximate said nozzle and a larger reservoir region interconnected to said nozzle region;

means, including piezoelectric bender means, for driving fluid from said reservoir region to said nozzle region and from said nozzle region through said nozzle to create an aerosol spray;

a flexible wall portion, included in said nozzle chamber and connected to said diaphragm, said wall portion responsive to deflection of said bender means for flexing to pressurize said fluid in said nozzle region of said nozzle chamber; and backflow restrictive means, formed between said flexible wall portion and the bottom of said concave portion of said diaphragm, for introducing fluid from said reservoir region to said nozzle region and restricting backflow from said nozzle region to said reservoir region.

49. A piezoelectric aerosol dispenser comprising:

a nozzle chamber for holding a fluid to be dispensed and a diaphragm forming at least a portion of said chamber and having an aerosol dispensing nozzle disposed therein, said chamber including a nozzle region proximate said nozzle and a larger reservoir region interconnected to said nozzle region;

means, including piezoelectric bender means, for driving fluid from said reservoir to said nozzle region and from said nozzle region through said nozzle to create an aerosol spray, said means for driving further including a pressurizing member attached at one end to said bender means, the opposite end being proximate to said nozzle, said nozzle region of said chamber being located between the opposite end of said pressure member and said nozzle; and backflow restrictive means, formed between the opposite end of said pressurizing member and said diaphragm, for introducing fluid from said reservoir region to said nozzle region and restricting backflow from said nozzle region to said reservoir region.

50. An aerosol dispenser comprising:

a nozzle chamber for holding a fluid to be dispensed and a diaphragm forming at least a portion of said chamber and having an aerosol dispensing nozzle disposed therein; said diaphragm further including a concave section within which said nozzle is centrally located, said chamber including a nozzle region proximate said nozzle and a larger reservoir region interconnected to said nozzle region;

means for driving fluid from said reservoir region to said nozzle region and from said nozzle region through said nozzle to create an aerosol spray; and backflow restrictive means, formed between the bottom of the concave section of said diaphragm and said means for driving, for introducing fluid from said reservoir region to said nozzle region and restricting backflow from said nozzle region to said reservoir region.

* * * * *